United States Patent
Ryan et al.

(10) Patent No.: US 9,918,508 B2
(45) Date of Patent: Mar. 20, 2018

(54) ATTACHABLE OPTICAL ELEMENT ARRANGEMENTS AND METHODS

(71) Applicant: ALPHAMICRON INCORPORATED, Kent, OH (US)

(72) Inventors: William Ryan, Kent, OH (US); Roy E. Miller, Stow, OH (US); Eui-Yeul Park, Hudson, OH (US); Bahman Taheri, Shaker Heights, OH (US)

(73) Assignee: ALPHAMICRON INCORPORATED, Kent, OH (US)

(*) Notice: Subject to any disclaimer, the term of this patent is extended or adjusted under 35 U.S.C. 154(b) by 294 days.

(21) Appl. No.: 14/441,641

(22) PCT Filed: Nov. 13, 2013

(86) PCT No.: PCT/US2013/069840
§ 371 (c)(1),
(2) Date: May 8, 2015

(87) PCT Pub. No.: WO2014/078380
PCT Pub. Date: May 22, 2014

(65) Prior Publication Data
US 2015/0272260 A1    Oct. 1, 2015

Related U.S. Application Data

(60) Provisional application No. 61/725,717, filed on Nov. 13, 2012.

(51) Int. Cl.
*G02F 1/1335*  (2006.01)
*A42B 3/22*    (2006.01)
(Continued)

(52) U.S. Cl.
CPC ............... *A42B 3/226* (2013.01); *A42B 3/24* (2013.01); *A61F 9/025* (2013.01);
(Continued)

(58) Field of Classification Search
None
See application file for complete search history.

(56) References Cited

U.S. PATENT DOCUMENTS 2,453,141 A    11/1948  Lange
3,395,406 A    8/1968   Smith
(Continued)

FOREIGN PATENT DOCUMENTS

CN    2800847 Y    8/2006    ............... A42B 3/18
CN    2800847 Y    8/2009    ............... A42B 3/18
(Continued)

OTHER PUBLICATIONS

European Search Report dated Nov. 22, 2016 in related application No. 13854381.4.
(Continued)

*Primary Examiner* — Richard Kim
(74) *Attorney, Agent, or Firm* — Renner Kenner Greive Bobak Taylor & Weber

(57) ABSTRACT

Described is a kit, an optical insert assembly and a method for attaching an optical insert to a viewing lens of an eye-shielding device. The kit includes an optical insert with an outer perimeter, and a flexible border attachment element with an inner periphery area extending inward of the outer perimeter of the optical insert, and an outer periphery area extending outward of the outer perimeter of the optical insert, and having a first adhesive area for attachment to the optical insert and a second adhesive area for attachment to the viewing lens. When attached, the border attachment element defines a buffer zone spanning the inner periphery and outer periphery areas. The optical insert assembly includes the elements of the kits described herein, attached to a viewing lens of an eye-shielding device.

20 Claims, 8 Drawing Sheets

(51) Int. Cl.
*A61F 9/02* (2006.01)
*A42B 3/24* (2006.01)
*B32B 37/00* (2006.01)
*B32B 37/12* (2006.01)
*B32B 37/18* (2006.01)
*G02C 7/10* (2006.01)

(52) U.S. Cl.
CPC .......... *B32B 37/0076* (2013.01); *B32B 37/12* (2013.01); *B32B 37/18* (2013.01); *G02C 7/101* (2013.01); *B32B 2307/412* (2013.01); *B32B 2457/202* (2013.01); *B32B 2551/00* (2013.01); *B32B 2571/00* (2013.01); *Y10T 156/10* (2015.01)

(56) References Cited

U.S. PATENT DOCUMENTS

| | | | |
|---|---|---|---|
| D214,013 S | 5/1969 | Jones | D29/110 |
| 3,686,690 A | 8/1972 | Webb | 2/9 |
| D227,819 S | 7/1973 | Kotzar | D29/110 |
| D228,700 S | 10/1973 | Gager | D29/110 |
| 4,047,249 A | 9/1977 | Booth | 2/10 |
| D254,638 S | 4/1980 | Bay | D29/109 |
| 4,495,657 A | 1/1985 | Bay | 2/10 |
| 4,584,721 A | 4/1986 | Yamamoto | 2/424 |
| 4,863,244 A | 9/1989 | Fuerthbauer et al. | 350/332 |
| 4,919,520 A | 4/1990 | Okada et al. | 350/331 T |
| 5,000,544 A | 3/1991 | Staveley | 350/174 |
| 5,131,101 A | 7/1992 | Chin | 2/424 |
| 5,172,256 A | 12/1992 | Sethofer et al. | 359/77 |
| 5,177,816 A | 1/1993 | Schmidt et al. | 2/424 |
| D341,230 S | 11/1993 | Kamata | D29/107 |
| 5,315,099 A | 5/1994 | Gunz et al. | 250/201.1 |
| 5,343,313 A | 8/1994 | Fergason | 359/83 |
| 5,471,036 A | 11/1995 | Sperbeck | 219/522 |
| D370,310 S | 5/1996 | Reuber et al. | D29/110 |
| D373,223 S | 8/1996 | Pernicka et al. | D29/110 |
| D376,674 S | 12/1996 | Kamata | D29/107 |
| D380,873 S | 7/1997 | Reuber | D29/110 |
| 5,642,530 A | 7/1997 | Parks | 2/435 |
| 5,671,483 A | 9/1997 | Rueber | 2/424 |
| D392,073 S | 3/1998 | Lashely | D29/122 |
| 5,756,010 A | 5/1998 | Appell et al. | 252/589 |
| 5,765,235 A | 6/1998 | Arnold | 2/424 |
| 5,802,622 A | 9/1998 | Baharad | 2/434 |
| D404,848 S | 1/1999 | Banuchi | D29/110 |
| D411,900 S | 7/1999 | Puleo | D29/107 |
| 5,959,705 A | 9/1999 | Fergason | 349/14 |
| D416,649 S | 11/1999 | Burns et al. | D29/110 |
| D418,255 S | 12/1999 | Hohdorf | D29/107 |
| 6,006,366 A | 12/1999 | Vondrak | 2/424 |
| 6,059,462 A | 5/2000 | Finak et al. | 385/73 |
| 6,101,256 A | 8/2000 | Steelman | 381/91 |
| 6,102,033 A | 8/2000 | Baribeau | 128/201.24 |
| 6,239,778 B1 | 5/2001 | Palffy-Muhoray et al. | 35/87 |
| D451,643 S | 12/2001 | Kalhok | D29/107 |
| 6,324,702 B1 | 12/2001 | Spindelbalker | 2/434 |
| D454,667 S | 3/2002 | Chartrand et al. | D29/110 |
| 6,405,373 B1 | 6/2002 | Grau | 2/15 |
| 6,493,128 B1 | 12/2002 | Agrawal et al. | 359/265 |
| 6,606,751 B1 | 8/2003 | Kalhok et al. | 2/424 |
| D481,173 S | 10/2003 | Alexander et al. | D29/110 |
| 6,690,495 B1 | 2/2004 | Kosa et al. | 359/86 |
| 6,832,393 B2 | 12/2004 | Folkesson | 2/410 |
| 6,886,183 B2 | 5/2005 | Dehaan et al. | 2/6.7 |
| 6,922,850 B1 | 8/2005 | Arnold | 2/424 |
| 6,999,220 B2 | 2/2006 | Kosa et al. | 359/241 |
| 7,007,306 B2 | 3/2006 | Howard et al. | 2/9 |
| 7,036,152 B2 | 5/2006 | Gafforio et al. | 2/15 |
| 7,102,602 B2 | 9/2006 | Kim et al. | 345/87 |
| D536,833 S | 2/2007 | Broersma | D29/107 |
| 7,303,302 B2 | 12/2007 | Harris | 362/105 |
| D564,135 S | 3/2008 | Cherry et al. | D29/108 |
| 7,342,210 B2 | 3/2008 | Fergason | 250/206 |
| D569,557 S | 5/2008 | Cho | D29/122 |
| D589,211 S | 3/2009 | Stevens et al. | D29/110 |
| D611,659 S | 3/2010 | Isobe | D29/122 |
| D627,108 S | 11/2010 | Blauer | D29/110 |
| 7,936,496 B2 | 5/2011 | Kosa et al. | 359/245 |
| D645,211 S | 9/2011 | Hill | D29/110 |
| 8,011,026 B2 | 9/2011 | Stevens | 2/427 |
| D658,812 S | 5/2012 | Miller et al. | D29/107 |
| D660,521 S | 5/2012 | Juhlin et al. | D29/122 |
| D661,841 S | 6/2012 | Klotz et al. | D29/109 |
| D662,261 S | 6/2012 | Klotz et al. | D29/109 |
| D669,639 S | 10/2012 | Klotz et al. | D29/110 |
| D675,786 S | 2/2013 | Klotz et al. | D29/110 |
| D675,787 S | 2/2013 | Klotz et al. | D29/110 |
| D675,788 S | 2/2013 | Klotz et al. | D29/110 |
| D677,008 S | 2/2013 | Klotz et al. | D29/110 |
| D677,435 S | 3/2013 | Klotz et al. | D29/110 |
| 2002/0191148 A1 | 12/2002 | Sheldon et al. | 351/62 |
| 2003/0052838 A1 | 3/2003 | Kim et al. | 345/32 |
| 2004/0221375 A1 | 11/2004 | Douglas | 2/424 |
| 2005/0002108 A1 | 1/2005 | Wilson et al. | 359/630 |
| 2005/0007504 A1 | 1/2005 | Fergason | 349/14 |
| 2005/0007506 A1 | 1/2005 | Farris et al. | 349/16 |
| 2005/0068762 A1 | 3/2005 | Post et al. | 362/105 |
| 2006/0293092 A1 | 12/2006 | Yard et al. | 455/575.2 |
| 2007/0151600 A1 | 7/2007 | Li et al. | 136/263 |
| 2007/0153354 A1 | 7/2007 | Duston et al. | 359/245 |
| 2008/0013000 A1 | 1/2008 | Park et al. | 349/13 |
| 2009/0100577 A1 | 4/2009 | Kobayashi et al. | 2/436 |
| 2010/0253603 A1 | 10/2010 | Righi et al. | 345/8 |
| 2011/0283431 A1 | 11/2011 | Miller, IV et al. | 2/10 |
| 2012/0038841 A1 | 2/2012 | Taheri et al. | 349/25 |
| 2012/0102628 A1 | 5/2012 | Righi et al. | 2/243.1 |
| 2012/0218301 A1 | 8/2012 | Miller | 345/633 |

FOREIGN PATENT DOCUMENTS

| | | | |
|---|---|---|---|
| JP | 56-111828 A | 3/1981 | |
| JP | S62-121420 | 6/1987 | ............... G02C 7/10 |
| JP | S63-118123 | 5/1988 | ............... G02F 1/13 |
| JP | S64-10721 | 1/1989 | ............... G02F 1/13 |
| JP | 11-160659 | 6/1999 | ............... G02C 7/10 |
| JP | 2005-97823 | 4/2005 | ............... A42B 3/24 |
| WO | WO 01/13750 A1 | 3/2001 | ............... A42B 3/24 |
| WO | WO 2008/033290 | 3/2008 | |
| WO | WO 2008/075286 | 6/2008 | |
| WO | WO 2010/088596 A1 | 8/2010 | ........... G02F 1/1335 |

OTHER PUBLICATIONS http://pinlockusa.net/; Pinlock, USA; 2012, The month and year of publication is believed to be sufficiently earlier than the effective U.S. priority filing date so that the particular month is not in issue.
http://www.fogcitysolutions.com/; Fog City; 2012, The month and year of publication is believed to be sufficiently earlier than the effective U.S. priority filing date so that the particular month is not in issue.
http://Inx.progrip.com/site/category-lenses; Pastiche Cassano, Italy; 2012, The month and year of publication is believed to be sufficiently earlier than the effective U.S. priority filing date so that the particular month is not in issue.
http://invisionvisorinserts.com/?product=hyper-shield-clear-for=arai; Maric Performance LLC; 2012, The month and year of publication is believed to be sufficiently earlier than the effective U.S. priority filing date so that the particular month is not in issue.
http://invisionvisorinserts.com/?product=speed-tint: Maric Performance LLC; 2012, The month and year of publication is believed to be sufficiently earlier than the effective U.S. priority filing date so that the particular month is not in issue.
http://www.skullskins.net/; SkullSkins; 2012, The month and year of publication is believed to be sufficiently earlier than the effective U.S. priority filing date so that the particular month is not in issue.
International Search Report dated Apr. 8, 2014 in corresponding application No. PCT/US2013/069840.
Written Opinion dated Apr. 8, 2014 in corresponding application No. PCT/US2013/069840.

(56) References Cited

OTHER PUBLICATIONS

Office Action dated May 9, 2013 in related U.S. Appl. No. 29/437,001.
http://bo.aving.net/16767/a_num/114202;"*Helmet Visor Insert, capable of adjusting its tint electrically for motorcycle*;" AVING Global news network; Feb. 3, 2009.
Office Action dated Jul. 5, 2013 in corresponding Chinese application No. 201080006113.2.
Office Action dated Mar. 5, 2014 in corresponding Chinese application No. 201080006113.2.
Office Action dated May 13, 2014 in corresponding Chinese application No. 201080006113.2.
Office Action dated Oct. 23, 2014 in corresponding Chinese application No. 201080006113.2.
Extended European Search Report dated Sep. 17, 2012 in corresponding application No. 10736520.7.
Office Action dated Dec. 15, 2013 in corresponding Japanese application No. 2011-548370.
Office Action dated Sep. 9, 2014 in corresponding Japanese application No. 2011-548370.
Office Action dated Mar. 31, 2015 in corresponding Korean application No. 10-2011-7020099.
"*MIT opens new "window" on solar energy*" Thomson, Elizabeth A.; Jul. 10, 2008 http://www.mit.edu/newsoffice/2008/solarcells-0710.html.
"*High Efficiency Organic Solar Concentrators for Photovoltaics*" Currie et al.; Science, vol. 321, Jul. 11, 2008; pp. 226-228.
"*MIT Brainstorms Alternative Energies*" Photonics Spectra; Oct. 2008; pp. 46-47.
International Search Report in related application No. PCT/US2010/022723 dated Mar. 16, 2010.
Written Opinion in related application No. PCT/US20108/022723 dated Mar. 16, 2010.
International Search Report in related application No. PCT/US2010/032396 dated Jun. 10, 2010.
Written Opinion in related application No. PCT/US2010/032396 dated Jun. 10, 2010.
Office Action dated Nov. 29, 2013 in related U.S. Appl. No. 13/146,657.
Response filed Mar. 28, 2014 in related U.S. Appl. No. 13/146,657.
Office Action dated Aug. 20, 2014 in related U.S. Appl. No. 13/146,657.
Response filed Jan. 20, 2015 in related U.S. Appl. No. 13/146,657.
Office Action dated Mar. 4, 2015 in related U.S. Appl. No. 13/146,657.
Response filed Jun. 4, 2015 in related U.S. Appl. No. 13/146,657.

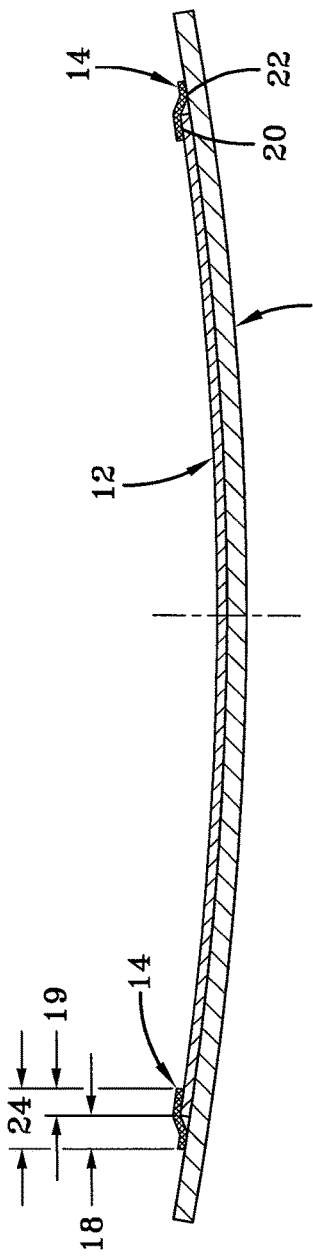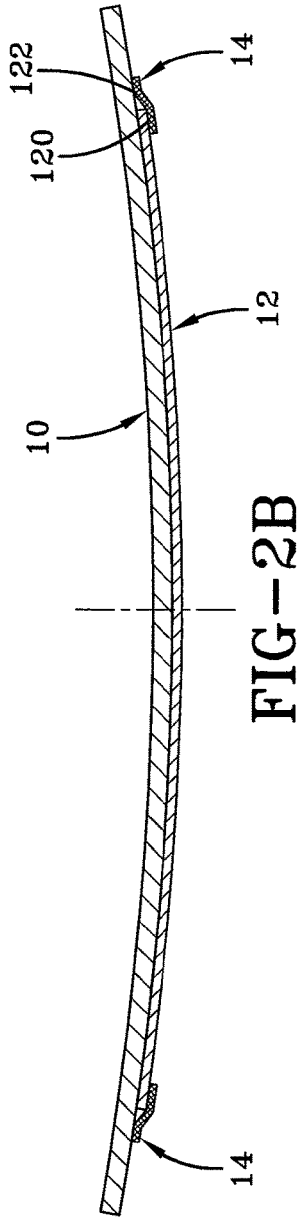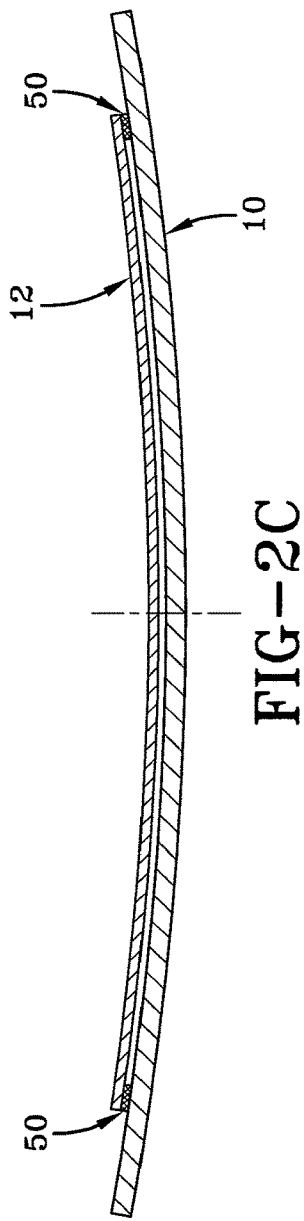

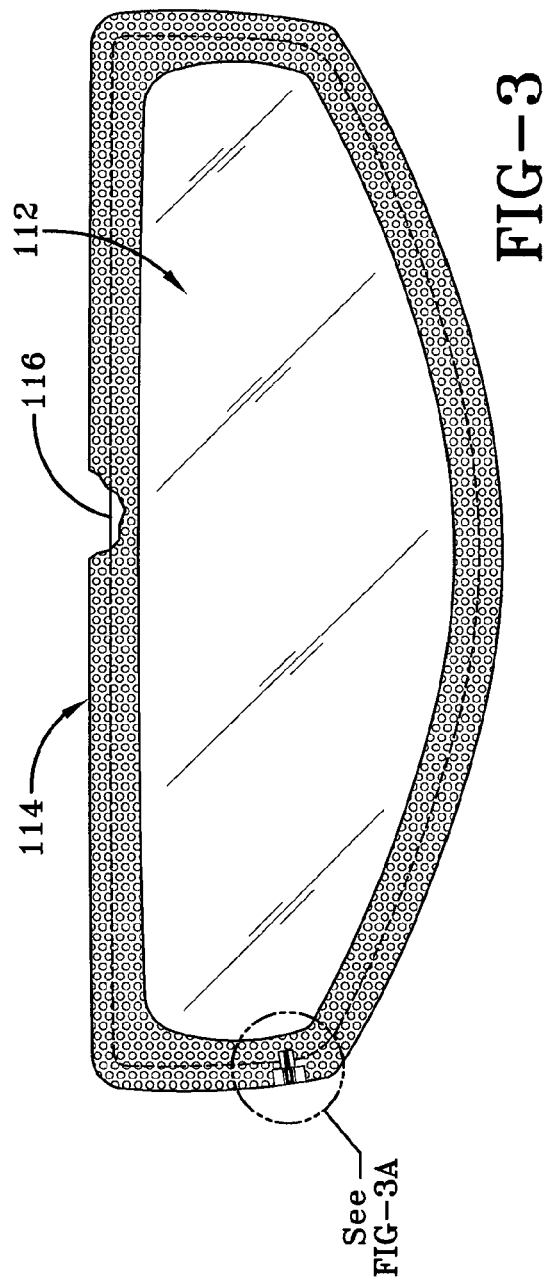
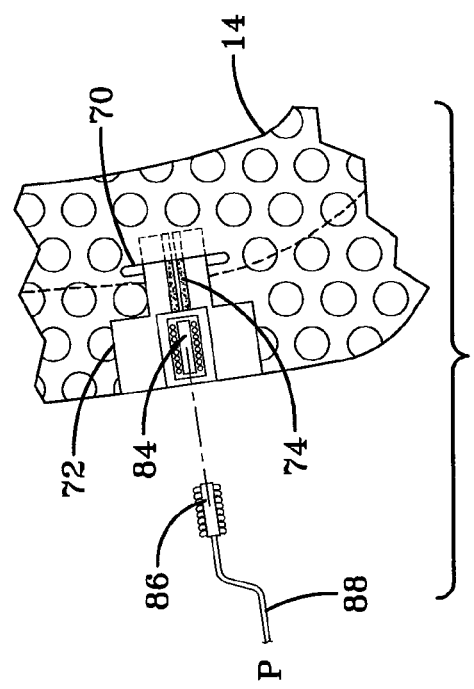
FIG-3
FIG-3A

ATTACHABLE OPTICAL ELEMENT ARRANGEMENTS AND METHODS

CROSS-REFERENCE TO RELATED APPLICATIONS

This application is a § 371 application of International patent application number PCT/US2013/069840 filed Nov. 13, 2013, which claims the benefit of U.S. Provisional Application Ser. No. 61/725,717 filed Nov. 13, 2012, which are incorporated herein by reference.

TECHNICAL FIELD

The present invention is directed to optical elements and their methods of assembly. Specifically, the present invention is directed to visors, goggles and other eye-shielding devices, and how optical elements are attached or otherwise secured to those devices.

BACKGROUND

Protective and performance enhancing helmet visors, goggles, and other such eye-shielding devices often provide protection for a wearer's eyes while maintaining or enhancing optical functionality for the wearer, for example, by magnifying, clarifying, darkening, tinting, or lightening ("bleaching") light transmission through the device. In many applications, such as motorcycle helmets, the eye-shielding device such as a visor is configured to match an opening in the helmet for the visor. In particular, the visor and helmet are designed to allow the user to seamlessly pivot the visor up or down. To avoid water penetration between the visor and helmet, the helmet is typically equipped with an elastic gasket which presses against the visor to create a tight seal. To enhance the capability of an eye-shielding device in a variety of conditions, including, for example, fog, condensation, sun glare, or darkness, an enhancing secondary lens (insert) can be used.

While the insert lens may be integrated into an eye-shielding device, in some instances, the insert may be provided as a separate attachment for assembly with or installation on an existing eye-shielding device, for example, for after-market or end user installation.

Typically, an optical insert is configured to fit various sizes and shapes of helmet visors. However, addition or presence of an insert presents several limitations. First, if a flat (non-curved or two-dimensional) optical insert is used, it may not fit a double or multiple curved viewing lens of an eye-shielding device, thus limiting the use of such an optical insert. Second, an insert will create a thickness variation which can significantly hinder the operation of the helmet gasket. In other words, if the insert is large, it can interfere with the sealing properties between the visor and the helmet gasket. On the other hand, if it is smaller than the visor, it may interfere with seamless movement of the visor. For example, the insert may catch the gasket as the user tries to pivot the visor up above the opening. To avoid this, the insert must be sized such that it can fit within the clearance created between the gasket and the visor as the visor is pivoted up. However, this sizing limitation can result in light leakage between the visor insert and the gasket, which can be highly undesirable. This issue has not been addressed with current inserts. Current inserts use either foam or a mechanical clip to hold the insert in place. And to avoid the interference with the gasket, the insert is typically much smaller than the visor.

Thus, it is desirable to have an attachment mechanism that can allow attachment of an optical insert without the limitation associated with the curvature of the visor or the gasket of the helmet, or both.

SUMMARY

Disclosed herein are optical insert assemblies, kits, and methods for attaching an optical insert to a viewing lens of an eye-shielding device.

The kit includes: an optical insert with an outer perimeter, and a flexible border attachment element with an inner and outer periphery, sized such that: at least a portion of its inner periphery extends inward of the outer perimeter of the flexible optical insert defining an "inner periphery area", and at least a portion of its outer periphery extends outward of the outer perimeter of the flexible optical insert defining an "outer periphery area". The border attachment element has a first adhesive area for attachment to the optical insert and a second adhesive area for attachment to the viewing lens of the face shielding device. When attached, the border attachment element defines a buffer zone spanning the border attachment element's inner periphery area (i.e. the portion of its inner periphery that extends inward and covers the optical insert), and outer periphery area (i.e. the portion of its outer periphery that extends beyond the outer perimeter of the optical insert).

The optical insert assembly includes all the elements of the kits described herein, attached to a viewing lens of an eye-shielding device.

The buffer zone may surround only a portion of the outer perimeter of the optical insert or, alternatively, may surround the entire outer perimeter of the optical insert.

The border attachment element is made of a flexible material which, in some examples, may be capable of stretching in one or more dimensions for better conformance to a curved surface of the viewing lens. The border attachment element can be clear, tinted or colored. In some embodiments, the border attachment element may have an area that is printed with a pattern, shape, logo, or any desirable design "printed" on its outside area, its inside area, or both.

In some embodiments, the border attachment element includes a perforated area or is made of a perforated sheet.

In some embodiments, the perforated area or sheet contains an array of perforated shapes (e.g. circles, triangles, squares, hexagons, etc.) that forms a "mesh screen" having a "hole to solid material" ratio of from 10:90, 20:80, 30:70, 40:60, 50:50, 60:40, 70:30, 80:20, 90:10 or any size in between. Preferably the hole to solid ratio is from 50:50 to 70:30, or any size in between. In some embodiments, at least a portion of the buffer zone comprises a pattern of opaque elements (e.g. circles, triangles, squares, hexagons, etc.) sized and spaced to provide a light filtering effect in the buffer zone.

In some examples, the pattern of the opaque elements form a mesh screen having a clear to opaque ratio of from 10:90, 20:80, 30:70, 40:60, 50:50, 60:40, 70:30, 80:20, 90:10 or any size in between. Preferably the clear to opaque ratio is from 50:50 to 70:30, or any size in between.

In some of the embodiments above, when the optical insert is secured to the inner surface of the viewing lens of an eye-shielding device by the border attachment element, the non-adhesive surface of the border attachment element in the buffer zone forms a ramped area between the inner surface of the optical insert and the inner surface of the viewing lens. This ramped area reduces interference between the insert and/or its edge and a device frame or gasket (e.g. a goggle frame or a helmet gasket).

In some embodiments, the border attachment has a thickness less than that of the optical insert such that it does not interfere with a helmet gasket during the movement of the visor.

The eye-shielding device is any device with a clear viewing area worn to protect the eyes. In some example, the eye-shielding device is a helmet visor, or goggle (e.g. sports goggle, ski goggle, paintball goggle, etc).

The optical insert may be any flexible plastic insert that can be attached to the viewing area of an eye-shielding device and which can alter or enhance the performance or optical properties of the eye-shielding device by providing an added function, e.g. an anti-fog function, a tinting function, a light-attenuating function (e.g. a photochromic, electrochromic or liquid crystal light attenuating device or the like), an anti-glare function, a decorative function, or a combination of any of the above, or any beneficial function.

The first and/or second adhesive areas of the border attachment element may comprise a permanent adhesive, or an adhesive configured for detachable attachment of the border attachment element to the optical insert, or the viewing lens, or both. For example, the adhesive areas may be configured so that the optical insert may be permanently attached to first adhesive area, but the second adhesive area may be detachably attached to the viewing lens. In other embodiments, the first and second adhesive areas may be configured so as to provide permanent attachment to the optical insert, the viewing lens or to both.

Also contemplated herein are various configurations for attachment of the border attachment element to the optical insert and viewing lens so that the first and second adhesive areas may be on the same surface, or on opposite surfaces from each other.

In some embodiments, the optical insert includes a flexible light attenuating element. Such an element may be "active" (i.e. need a voltage applied to it to operate), such as a liquid crystal or electrochromic device. In some examples, the element may be "passive" (i.e. operate without the requirement for a voltage), such as a photochromic device or the like.

In some embodiments, the flexible light attenuating element includes an electronically controlled liquid crystal cell and a controller electrically connected to the liquid crystal cell and configured to selectively supply a voltage across the liquid crystal cell. In some embodiments, the controller is an integral part of the optical insert while in other embodiments; the controller may be a separate device. In the latter case, the kit or optical insert assembly may include the separate controller device, that can be attached to the viewing lens or the eye-shielding device itself (e.g. its frame, helmet shell, etc.).

The controller may be operated automatically, semi-automatically, or exclusively by user input (manually or by a remote control device), or any combination of the above (e.g. have both an automatic and a manual mode, etc.). The activation device may be part of the controller device, or a separate device. Accordingly, the kit or optical insert assembly may further include a manually operable activation device electrically or remotely connected with the controller for selectively adjusting the voltage across the liquid crystal cell.

In some embodiments, the optical insert may include a protective film for improved structural integrity (e.g. to add strength) or ease of handling of the optical insert.

Also provided herein are methods for attaching an optical insert to a viewing lens of an eye-shielding device. The method includes providing a viewing lens; providing an optical insert having an outer perimeter; providing a border attachment element having an inner periphery area and an outer periphery area as described above, the border attachment element having a first adhesive area for attachment to the optical insert and a second adhesive area for attachment to the viewing lens. The method further includes adhering the first adhesive area to the optical insert and/or adhering the second adhesive area to the viewing lens so as to create a buffer zone spanning the inner periphery area and the outer periphery area.

In some embodiments of the method, the optical insert and the border attachment element may have been pre-adhered, so that the end user would only need to attach the pre-adhered assembly to the viewing lens.

The methods described herein use the kits and examples enumerated above and result in the optical insert assemblies described herein. Therefore, all the elements recited for the optical insert assemblies, kits and methods are interchangeable and apply to each described invention.

For example, where the optical insert assembly or kit includes an electronically controlled light attenuating device (such as a liquid crystal cell), the method may further include securing to the viewing lens, or the eye-shielding device, its frame, helmet, etc., a controller and/or an activation device electrically connected with the liquid crystal cell for selectively adjusting the voltage across the liquid crystal cell, as described above In some embodiments, the method includes detachably adhering the second adhesive area to the eye-shielding device, so that the optical insert may be removed when not needed, or for replacement or repair purposes, etc. In such cases, the optical insert may be permanently adhered to the border attachment element, so that by separating the border attachment element from the viewing lens, the optical insert will also be removed. In other instances, the optical insert itself may be detachably attached to the border attachment element. In this example, different border attachment elements may be used with the same optical insert, e.g. for different conditions or as desired by fashion, etc. In other embodiments, the first and second adhesive areas may be configured so as to provide permanent attachment to the optical insert, the eye-shielding device or to both.

In some examples, where the border attachment element includes a perforated sheet or area or is flexible such that it can be stretched, adhering the border attachment element to the viewing lens may involve stretching the border attachment element for better conformity to the shape of the viewing lens and therefore better attachment. For example, when attaching the optical insert to a curved helmet visor, the border attachment element may be stretched around a first axis bisecting a width of the perforated area and around a second axis perpendicular to the first axis and bisecting a height of the perforated area, such that the outer periphery of the adhesive area conforms to the viewing lens or visor having one or more axes of curvature. In this way, a flat optical insert may be successfully attached to a viewing area of an eye-shielding device that is curved, even when it is curved in more than one dimension (double- or multiple-curved lens).

BRIEF DESCRIPTION OF THE DRAWINGS

Features and advantages of the invention will become apparent from the following detailed description made with reference to the accompanying drawings, wherein:

FIGS. 2A and 2B show a cross-sectional schematic of the assembled optical insert and attachment element according to the invention. FIG. 2C shows a prior art cross-sectional schematic example of an optical insert attached to a viewing lens;

FIG. 3 is an elevational view of a border attachment element having an opening for protrusion of an interconnection tab through it, which is shown in the detailed view of FIG. 3A;

DETAILED DESCRIPTION OF THE DISCLOSURE

Figure 1A:
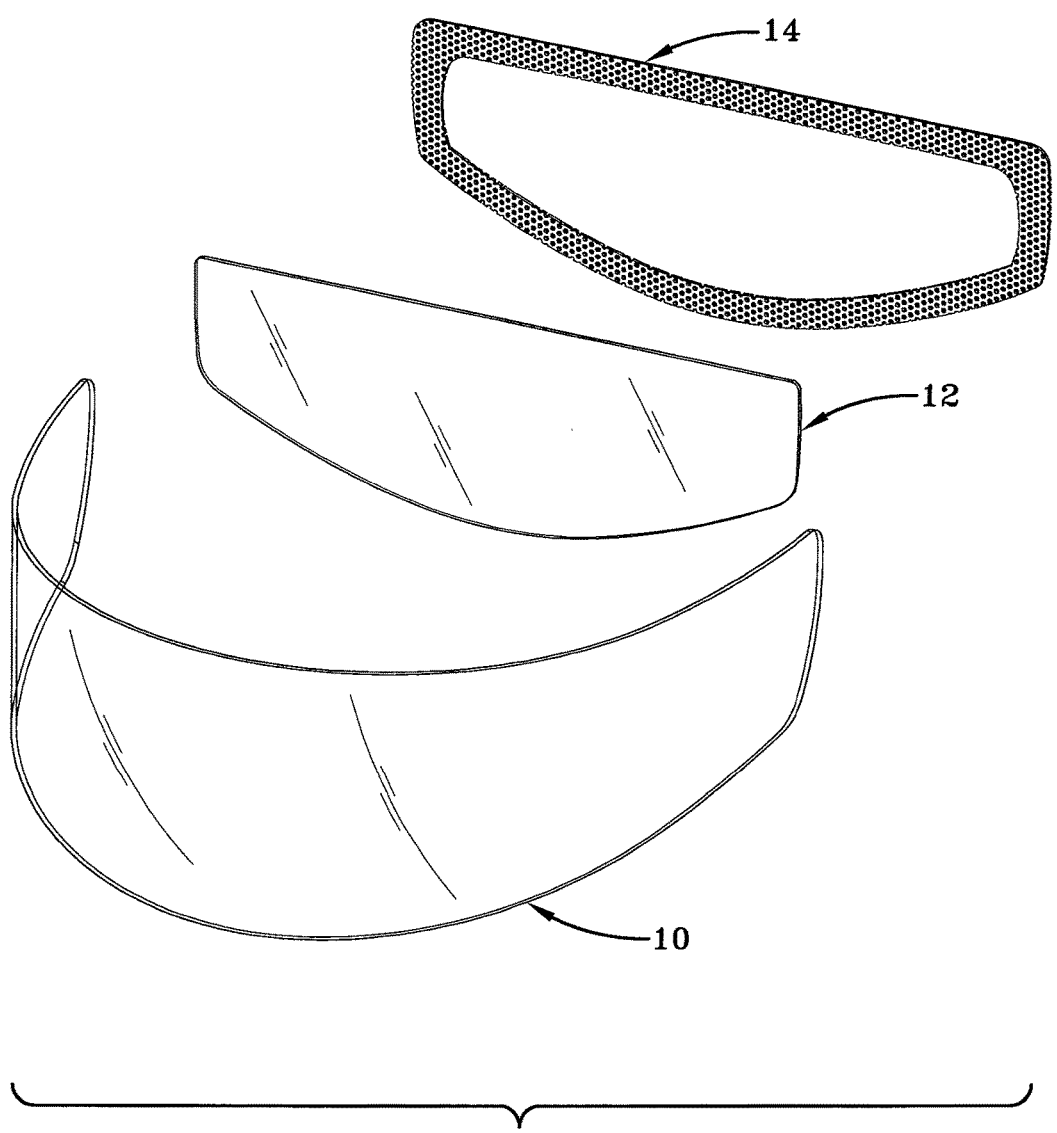
FIG. 1A is an exploded, perspective schematic diagram of a viewing lens, an optical insert and a border attachment element according to the invention.

The structures shown schematically in the drawings have parts that are examples of the elements recited in the apparatus claims. The illustrated structures thus include examples of how a person of ordinary skill in the art can make and use the claimed invention. It is described here to meet the enablement and written description requirements of the patent statute without imposing limitations that are not recited in the claims.

The present application contemplates optical insert assemblies, kits and methods for attaching an optical insert to a viewing lens of an eye-shielding device. The eye-shielding device is any device with a clear viewing area worn to protect the eyes. Examples include a protective helmet visor (e.g. for sports, racing, motorcycle, paintball helmets, etc.), or protective goggles (e.g. ski or other sports goggles, etc) and the like.

The optical insert may be any flexible plastic insert that can be attached to the viewing area of an eye-shielding device and which can alter or enhance the performance of the eye-shielding device by providing an added function, e.g. an anti-fog function, a tinting function, a light-attenuating function (e.g. a photochromic, electrochromic or liquid crystal light attenuating device or the like), an anti-glare function, a polarizing function, a UV protection function, or a combination of any of the above.

According to one aspect of the invention, a kit is provided for assembly with the viewing lens of an eye-shielding device (such as a helmet visor, or goggle). Such a kit may be manufactured as an after-market product for assembly by a retailer or an end user.

Figure 1B:
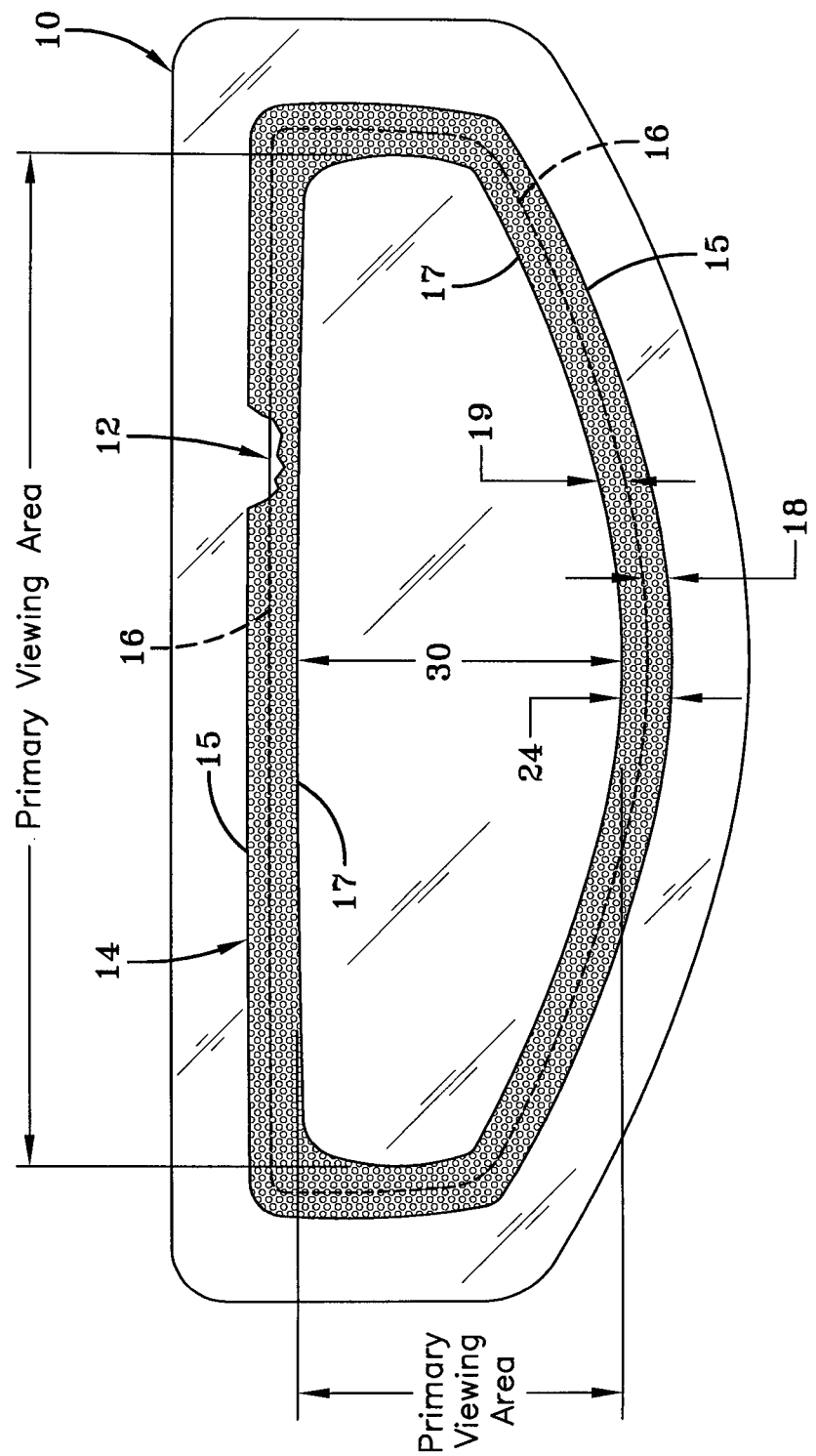
FIG. 1B is an elevational view, partially broken away, of the assembled optical insert, border attachment element and viewing lens as described herein.
Figure 4:
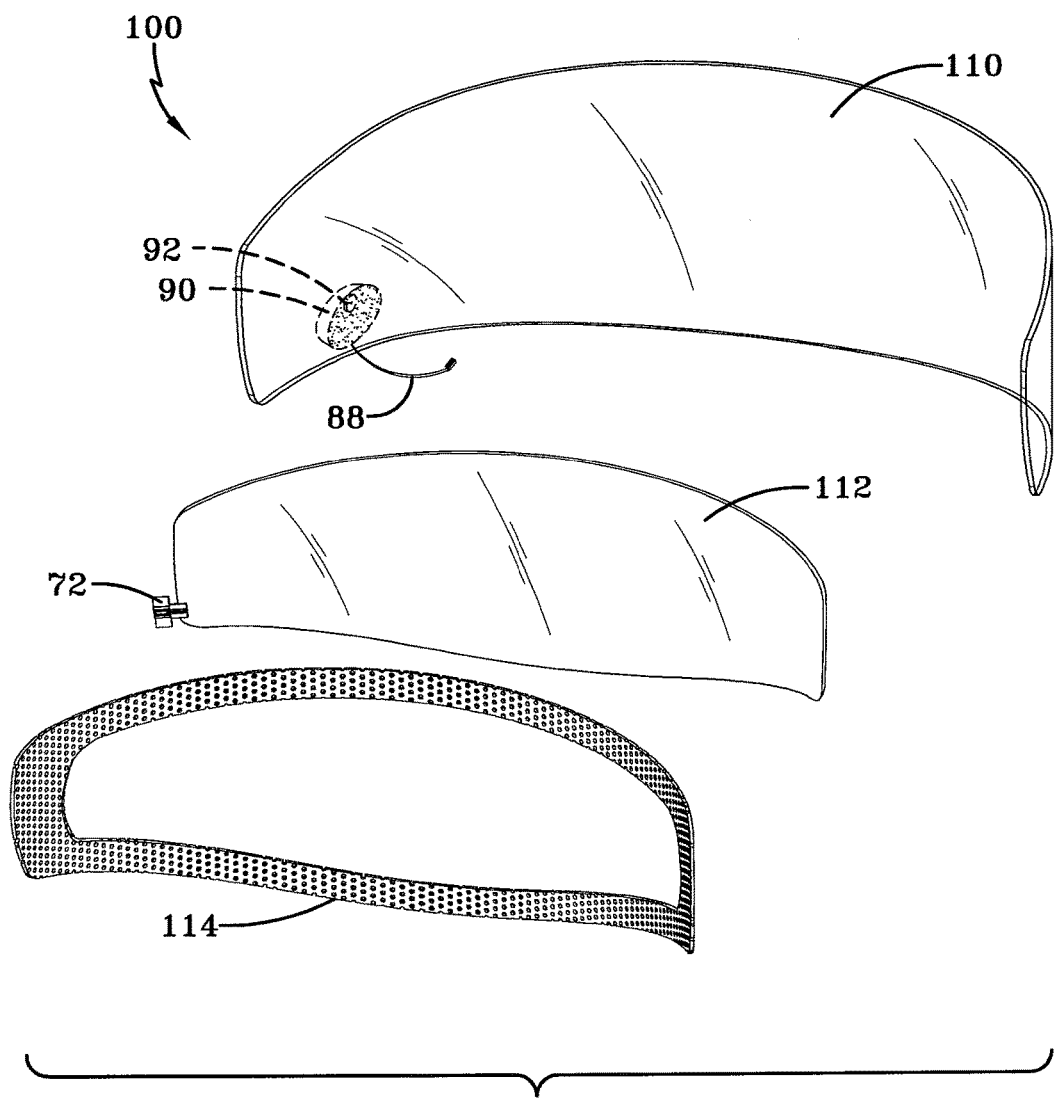
FIG. 4 is an inside perspective view of a helmet visor, a border attachment element, and an electronically controlled light attenuating optical insert and a separate controller, shown with the optical insert and border attachment element separated from the helmet visor.

As shown in FIGS. 1 and 2, the kit includes an optical insert 12 and a border attachment element 14. FIG. 1A shows the separate elements of the kit as well as the viewing lens 10 of an eye-shielding device before assembly. FIG. 1B shows the different elements after they have been assembled and attached to the viewing lens 10. The optical insert 12 has an outer perimeter 16. The border attachment element 14 has an outer periphery 15 and an inner periphery 17. At least a portion of the outer periphery 15 extends outside the outer perimeter 16, defining an "outer periphery area" 18. AT least a portion of the inner periphery 17 extends inward of the outer perimeter 16 of the optical insert 12. The area between the optical element's outer perimeter 16 and the border attachment element's inner periphery 17 forms an "inner periphery area" 19. The inner periphery area 19 covers part of the optical insert 12 to define a primary viewing area 30.

In one embodiment, shown in FIG. 2A, the border attachment element 14 has a first adhesive area 20 for attachment to the optical insert 12 and a second adhesive area 22 for attachment to the viewing lens.

When attached, the border attachment element 14 defines a buffer zone 24 which spans the outer periphery area 18 (i.e. the portion of the outer periphery that extends beyond the outer perimeter 16 of the optical insert 12) and the inner periphery area 19 (i.e. the portion of the outer periphery that extends inward of the outer perimeter 16). The buffer zone may surround only a portion of the primary viewing area, or, alternatively, may surround the entire primary viewing area (as shown in FIG. 1B). The buffer zone may be clear, tinted, colored, or include a pattern on at least a portion of its surface.

Traditionally, optical inserts configured to be attached to helmet visors or similar viewing lenses needed to have a gasket or peripheral foam or adhesive material for attachment to the visor to create a moisture barrier. This "gasket" often provided an opaque or optically unclear border area around the optical insert. (see FIG. 2C). Other optical insert designs employed mechanical means for attachment to a helmet visor, again resulting in unsightly attachment means that could be seen by the wearer or a viewer looking at the visor from the outside. However, using a border attachment element as described above removes the necessity for providing such a gasket, foam or border zone around the optical insert or providing attachment means directly on the optical insert. Although such a gasket or foam may be employed, it is not necessary and the optical insert can be configured to function without such a peripheral gasket or foam. Thus, the optical insert of the present invention may be provided with or without a gasket. In some examples, the buffer zone may be clear so that the user sees no abrupt "border" around the optical insert.

However, in some embodiments, at least a portion of the buffer zone 24 may include a pattern of opaque elements sized and spaced to provide a light filtering effect in at least a portion of the buffer zone. The opaque elements may be any pattern or color. In some examples, the pattern includes an opaque mesh pattern of repeating shapes (such as squares, triangles, circles, hexagons, etc.) having a "clear to opaque material" ratio of 10:90, 20:80, 30:70, 40:60, 50:50, 60:40, 70:30, 80:20, 90:10 or any size in between. Preferably the clear to opaque ratio is from 50:50 to 70:30, or any size in between. In some examples, the pattern is made of clear circular holes surrounded by opaque material. See FIG. 3. Other patterns can also be provided in any color, and in any configurations, e.g. to display images, logos, etc. as desired by the end-user. In some examples, the patterns or the color may be only on the outside surface of the border attachment element, i.e. so it is visible only from the outside. In other examples, the patterns/color may be on the inside surface (visible to the user) or on both surfaces (visible both to the user and an outside viewer).

The border attachment element is made of a flexible material which, in some examples, may be capable of stretching in one or more dimensions for better conformance to a curved surface of the viewing lens.

In some embodiments, the border attachment element 14 includes a perforated area or sheet. The perforated area or sheet, which may be made of any flexible plastic, can have an array of perforations sized and arranged to permit further stretching of the perforated area in two dimensions to permit attachment of a flat optical insert to a visor with different curvatures. This stretching may also make it possible to adhere a flexible but flat optical insert 12 to a visor's viewing area when the visor is curved in one or more dimensions.

In some examples, the pattern of perforations includes a mesh pattern of repeating shapes (such as squares, triangles, circles, hexagons, etc.) having a "hole to solid material" ratio of 10:90, 20:80, 30:70, 40:60, 50:50, 60:40, 70:30, 80:20, 90:10 or any size in between. Preferably the hole to solid ratio is from 5:50 to 70:30, or any size in between. In some examples, the "holes" are circular. See FIG. 3. The mesh screen may have any color, including a clear color, white (or opaque), black, or any color chosen by the user.

Adhesion of the optical insert 12 to the border attachment element 14 may be achieved in two ways, as shown in FIG. 2. FIG. 2A shows an arrangement where the first adhesive area 20 is used to attach to the inside surface of the optical insert 12 and the second adhesive area 22 is used to attach to the inside surface of the viewing lens 10. In this arrangement, border attachment element 14 forms a "ramp" between the optical insert 12 and the viewing lens 10. This "ramp" has the advantage of protecting the optical insert 12 and its edges from being bumped, dislodged or detached, for example if a helmet gasket around the viewing area of an eye-shielding device, or another object, accidentally hits against the outer perimeter of the optical insert. This is particularly useful where the optical insert is attached to a helmet visor or the like, where the visor moves (e.g. pivots up and down) in relation to the remainder of the helmet. For example, the ramped area, when provided on the upper and lower edges of the optical insert 12 on a motorcycle helmet, helps prevent abrasion of the edges of the optical insert by the helmet gasket when pivoting the helmet visor 10 between raised and lowered positions. When pivoting the helmet visor, the ramped area guides the gasket over the optical insert 12 and prevents direct engagement with the edge of the optical insert. In other embodiments, for example if the eye-shielding device is a goggle, the ramp can simplify handling the assembled optical insert —viewing lens and inserting in into the frame of the goggle without the frame hitting or bumping the edge of the optical insert. It should be noted that the figures are not to scale, and so for example, the border attachment element 14, which forms the ramp in FIG. 2, may be much thinner than the optical insert 12.

The "ramp" feature formed by the border attachment element, therefore, simplifies the assembling and attachment of the optical insert to the viewing lens, and protects the edges of the optical insert against being hit or bumped or displaced. Another advantage of the border attachment element is that it is no longer necessary to provide a foam or gasket around the inside surface of the optical insert (see FIG. 2C showing a prior art optical insert attached by means of a gasket or foam 50 to the viewing lens 10).

Another problem inherent in traditional models, where a gasket around the optical insert was used for attachment to the viewing lens (FIG. 2C), was that when a flat optical insert was flexed or bent to conform to a curved viewing lens, the gasket, which has a considerable thickness, as compared to the optical insert, would become strained or would "wrinkle", resulting in inferior attachment, or aesthetics, or both. The flexible border attachment element of the present invention circumvents that problem by eliminating, in some example, the need for the traditional gasket, and by being considerably more flexible than traditional gaskets, enhancing the aesthetics and the attachment quality.

FIG. 2B shows another embodiment where the optical insert 12 and border attachment element 14 are attached to the outside surface of the viewing lens 10 of an eye shielding device. In this arrangement, optical insert 12 is attached to a first adhesive area 120 and viewing lens 10 is attached to a second adhesive area 122. This arrangement can also make advantageous use of the "ramp" formed by the border attachment element 14, for example, if the assembled viewing lens and the optical insert need to be placed inside a frame, etc. (e.g. of a goggle).

In any of the embodiments described above (FIG. 2A-B), a uniform adhesive coating may be provided on the first and second adhesive areas so as to provide permanent attachment to the optical insert 12 and the viewing lens 10. Alternatively, the adhesive coating on the first and second adhesive areas may be configured to detachably attach to the optical insert 12 and the viewing lens 10.

Alternatively, the type of adhesive provided on the first and second adhesive areas may be different, so that one provides a permanent attachment while the other provides a detachable attachment, or vice versa. For example, the adhesives may be configured to provide a substantially permanent attachment of the border attachment element 14 to the optical insert 12, and a substantially detachable attachment of the border attachment element 14 to the viewing lens 10, allowing for removal, replacement, and/or repositioning of the optical insert-border attachment element assembly on the viewing lens or onto another viewing lens or device.

In other instances, the optical insert itself may be detachably attached to the border attachment element. In this example, different border attachment elements may be used with the same optical insert, e.g. for different conditions or as desired by fashion, etc.

In some embodiments, the kit may include a pre-assembled (pre-adhered) optical insert and border attachment element so the end user would only be required to attach the pre-assembled element to the viewing lens.

The term "detachable attachment" is defined as an attachment that nevertheless enables the end user to detach the objects if desired. Accordingly, an optical insert that is detachably attached may be removed by the end user without causing damage to the visor or to the optical insert. In contrast, "permanently attached" optical inserts or border attachment elements are not meant to be removed by the end user once they have been attached because such removal may cause damage to the viewing lens or the optical insert.

In any of the above described embodiments, the border attachment element can be clear, tinted or colored (e.g., to match the frame or helmet shell). In some embodiments, the border attachment element may have an area that is printed with a pattern, shape, image, logo, or any desirable design "printed" on its outside surface, its inside surface, or both. For example the non-adhesive area of border attachment element 14 may be provided in a dark color (e.g. grey or black) to provide a shading effect through the buffer zone area. The adhesive area of the border attachment element may be a similar color, or may be provided in other colors, or printed in a variety of suitable or desirable patterns, logos, or images.

In some embodiments, the optical inset is an anti-fog, anti-glare, polarizer or a tinted insert.

In some embodiments, the optical inset is a flexible light attenuating element. Light attenuating elements include any element where the element can change tint in response to light (e.g. photochromic) or an external stimulus (e.g. voltage or current). Examples of light attenuating elements include photochromic, electro-chromic, or liquid crystal elements, or the like.

An exemplary optical insert includes an electronically controllable variable light-attenuating liquid crystal cell that uses a guest-host solution comprising a host material and a light-absorbing dichroic dye guest. One such liquid crystal cell is described in detail in U.S. Pat. No. 6,239,778 (Taheri et al.), the entire disclosure of which is incorporated herein by reference. The liquid crystal cell selectively or automatically adjusts light absorption of the optical insert. Electrical signals delivered to the liquid crystal cell alter the orientation of a light attenuating dichroic dye dispersed in the liquid crystal cell, thereby altering the light attenuation or absorption of the liquid crystal cell. The light attenuating element includes a controller electrically connected to the liquid crystal cell and configured to selectively supply a voltage across the liquid crystal cell.

In summary, the liquid crystal cell includes spaced apart, opposed substrates forming a gap which contains a mixture of a liquid crystal or other electro-optic material host material (such as an electro-chromic or photochromic-dichroic material) and a guest dichroic dye material. The substrates may contain transparent electrode layers, which may be formed from indium tin oxide, conductive polymer or other appropriate conductive material, to allow for application of a voltage across a gap between the substrates. The material used for the substrates is a flexible plastic material. If required, an alignment layer may be disposed on each electrode layer or just one of the electrode layers. The alignment layers can align the liquid crystal molecules adjacent to the alignment layers, wherein the molecules are part of the liquid crystal material received between the substrates. The gap between the substrates is maintained by spacers, as is commonly known in the art.

The substrates, through their electrode layers, are connected to a controller (90) which typically includes a drive circuit, a power source and an activator or activation circuit. The control circuit applies a voltage and/or voltage waveform in an appropriate manner to change the orientation of the liquid crystal material. By changing the orientation of the liquid crystal material, various optical properties (e.g., absorption, no absorption, high transmission, low transmission, and states in between) may be obtained. Accordingly, the variable light-attenuating liquid crystal cell described herein can change tint, i.e. go from a "clear" state, where the optical element allows the maximum amount of light through, to a "tinted" state, where the optical element allows the minimal amount of light through, or in any state between the fully clear or fully tinted states. The absorption can be broad-band (i.e. absorbing across the entire visible spectrum) or across a selected band or region of the visible light spectrum. Additionally, the optical element may provide protection against UV light. In some examples, the variable light-attenuating liquid crystal cell used in some embodiments of the optical element is configured so that it is "fail-safe", i.e. it reverts to the clear state when there is no voltage applied across the liquid crystal cell. In an exemplary embodiment, the variable light-attenuating liquid crystal cell does not employ polarizers.

In other embodiments, the optical element may contain a photochromic-dichroic cell, containing a light-sensitive mixture comprising a fluid material and a photochromic dyestuff material, and a medium for carrying the mixture, wherein the mixture varies between a first condition and a second condition, the first condition letting substantially all light to pass through the mixture, and the second condition absorbing light passing through the mixture. The mixture containing a fluid (such as a liquid crystal) material and photochromic dyestuff material is described in greater detail in U.S. Pat. No. 6,999,220 (Kosa et al.), Device Exhibiting Photo-Induced Dichroism For Adaptive Anti-Glare Vision Protection, the entire disclosure of which is incorporated herein by reference. Such a mixture will exhibit photo-induced dichroism.

In some embodiments, the flexible light attenuating element includes an electronically controlled liquid crystal cell and a controller electrically connected to the liquid crystal cell and configured to selectively supply a voltage across the liquid crystal cell. In some embodiments, the controller is an integral part of the optical insert while in other embodiments; the controller may be a separate device. In the latter case, the kit or optical insert assembly may include the separate controller device, that can be attached to the viewing lens or the eye-shielding device itself (e.g. its frame, helmet shell, etc.).

When a controller is used to activate the optical element, a variety of electrical connections, controls, and power sources may be utilized, examples of which are described in U.S. Patent Application Pub. No. 2011/0283431 (Miller, I V et al.) and in U.S. Pat. No. 7,936,496, entitled INTERCONNECTION TAB USED WITH OPTICAL DEVICES, the entire disclosures of which are incorporated herein by reference.

The controller may be operated automatically, semi-automatically, or exclusively by user input (manually or by a remote control device), or any combination of the above (e.g. have both an automatic and a manual mode, etc.). The activation device may be part of the controller device, or a separate device. Accordingly, the kit or optical insert assembly may further include a manually operable activation device electrically or remotely connected with the controller for selectively adjusting the voltage across the liquid crystal cell.

The connection between the optical element substrates (or electrodes) and a controller may be achieved in a variety of ways known in the art. One example is illustrated in FIGS. 3-6, showing a viewing lens 110, an electronically controlled light attenuating element 112 and its electronic connection through the border attachment element 114. Accordingly, the border attachment element 114 has a slit or opening 70 through which an inter-connection tab 72 can pass through and protrude. The interconnection tab 72 contains a conductive via 74 which connects the electrode layers of the optical element 112 to a plug 84. The plug 84 mates with a socket 86, which is connected through a wire 88 with the controller 90. Alternative connection elements other than a wire can also be used, such as a flexible via, etc. This is an example of a disconnectable arrangement, which may be utilized, for example, to facilitate replacement of only one of the light attenuating element 112 and the controller 90, or to enable storage as separate components. In still other embodiments, a controller may be connected to the light attenuating element with leads on the drive circuit connected directly to the conductive tabs of the light attenuating element. This may also facilitate attachment of the controller to the eye-shielding device.

In some examples where the viewing lens is a helmet visor, to facilitate retrofitting the optical insert to the helmet visor, the wired connection 88 may be secured to the inner surface of the visor. Alternatively, the controller 90 can be secured to an outer surface of the visor 110, and the wired connection 88 may be extended over an outer edge (e.g., a lower edge, as shown in FIG. 5) of the visor 110, or may go through a hole in the visor.

Different mechanisms and configurations may be utilized to attach a controller to an eye-shielding device or its viewing lens, including mechanical, chemical, a combination of chemical/mechanical, friction or pressure, magnetic, hook and loop fastener (VELCRO®), or a combination thereof. In the illustrated example, the controller 90 is provided with an adhesive pad 92 for attachment to a surface of the helmet visor 110.

Figure 5:
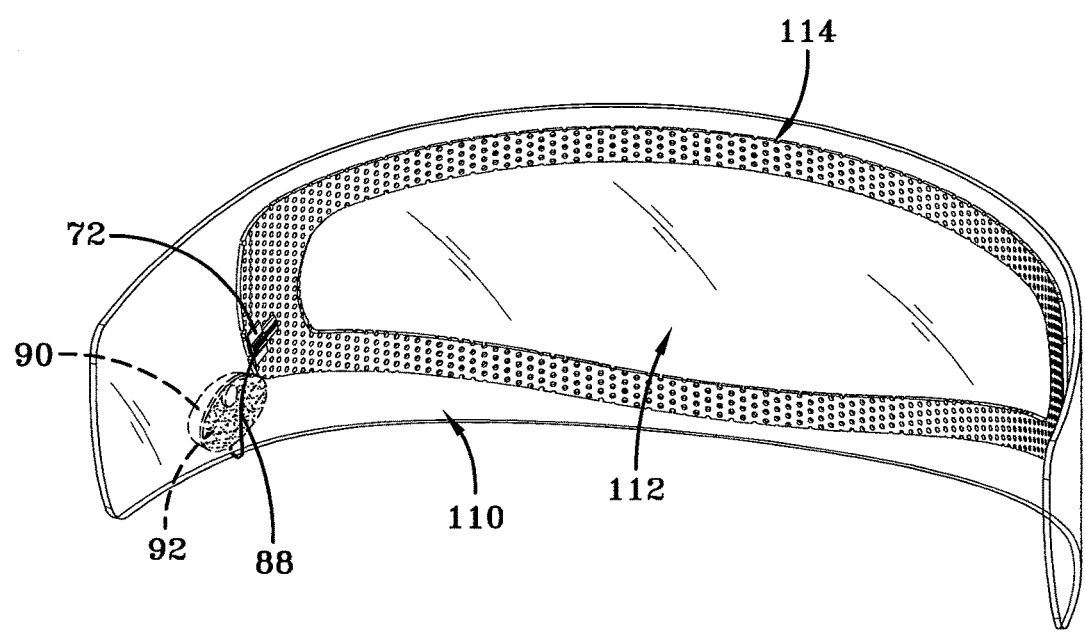
FIG. 5 is an inside perspective view of the border attachment element and optical insert of FIG. 4 attached to the helmet visor and controller.
Figure 6:
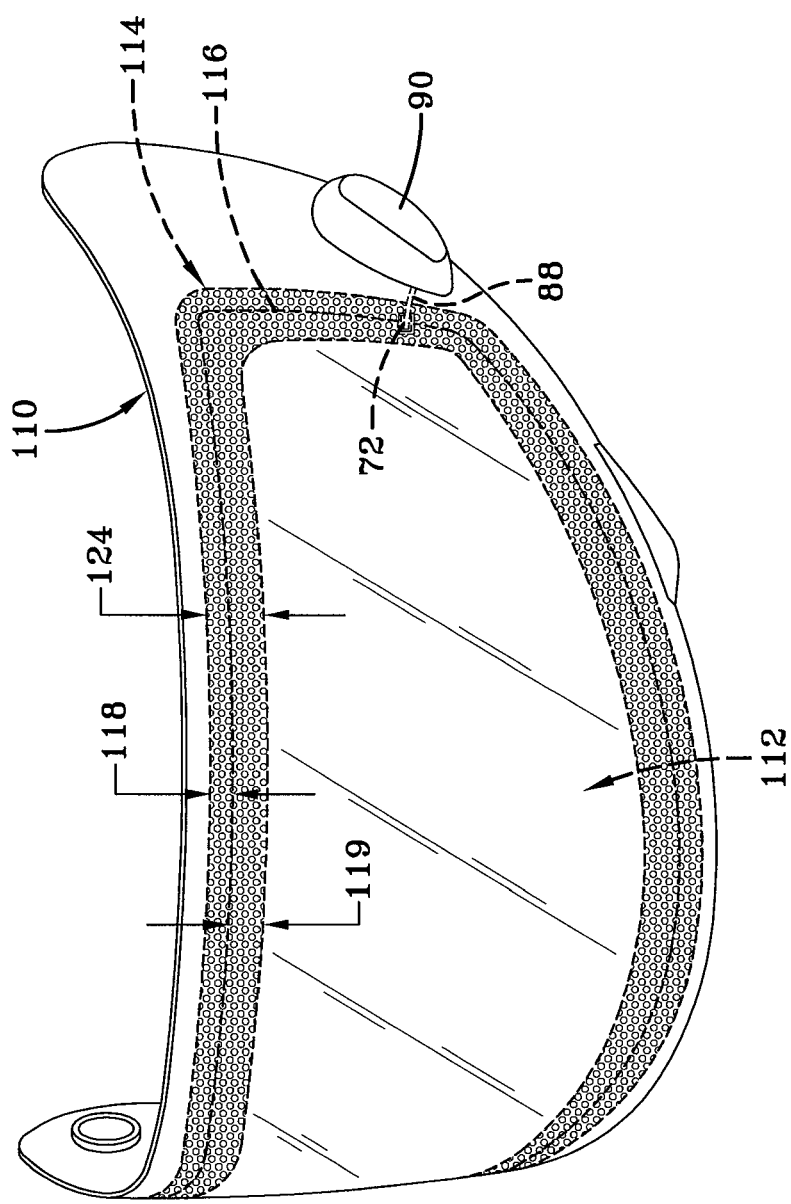
FIG. 6 is an outside perspective view of the optical insert assembly of FIG. 5.

FIG. 6 shows the arrangement of FIG. 5 as it appears to an outside viewer (i.e. viewed through the viewing lens 110). It also shows the outer periphery area 118, the inner periphery area 119, and the buffer zone 124 as viewed from the outside.

In some embodiments, such as the above described example, the controller is activated manually, so the optical element assembly or the kit further include a manually operable activation device electrically (or remotely) connected with the controller for selectively adjusting the voltage across the liquid crystal cell.

Figure 7:
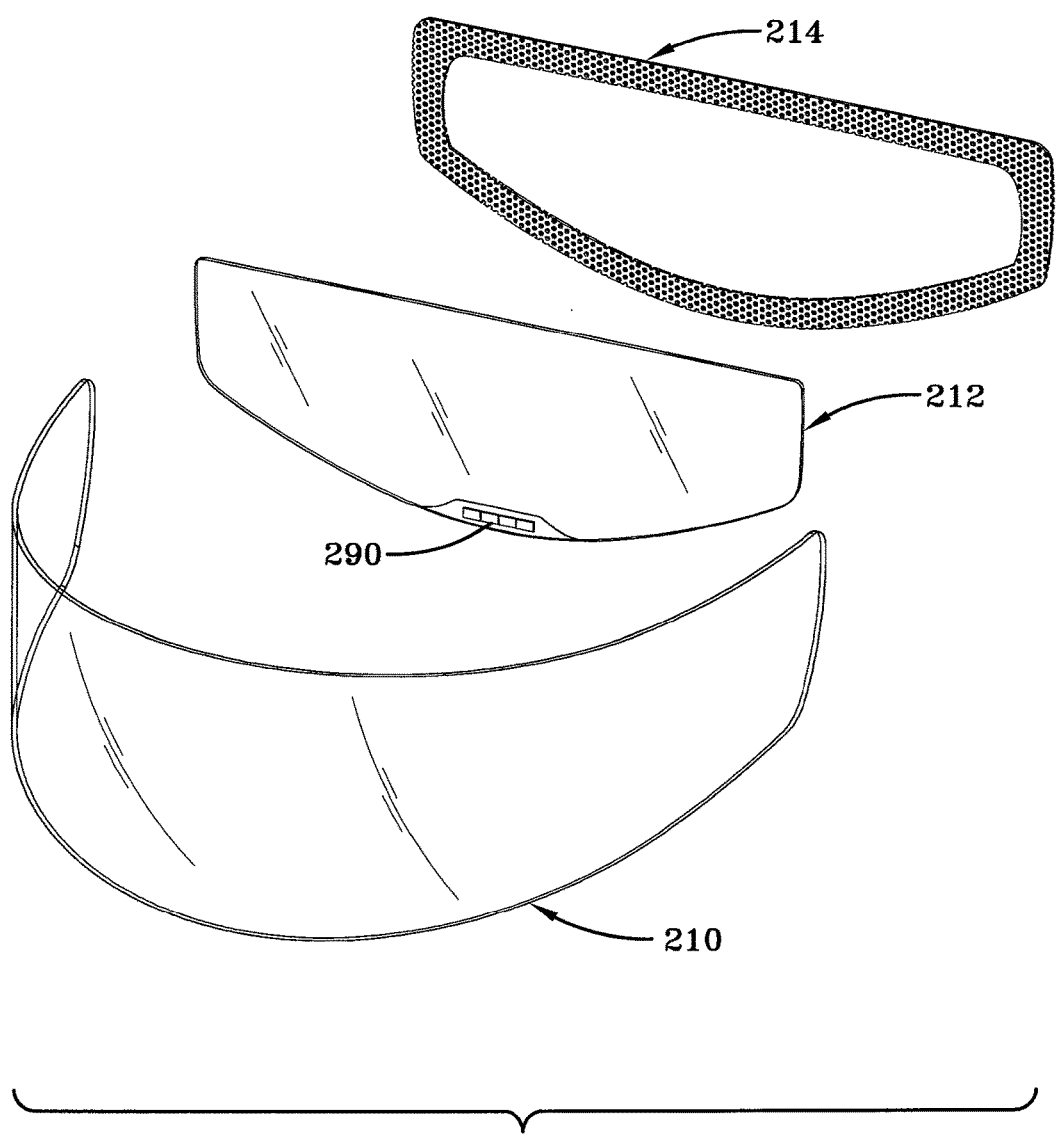
FIG. 7 is an exploded, perspective view of a helmet visor, a border attachment element, and an electronically controlled light attenuating optical insert with an integrated controller, shown with the optical insert and border attachment element separated from the helmet visor.

In other embodiments, the activation device or controller may be operated automatically, semi-automatically, or by a combination of the above. For example, in FIG. 7, a viewing lens 210 is shown together with an optical element or insert 212 and a border attachment element 214. The optical element 212 includes a controller 290. As can be seen in this example, the controller 290 is an integral part of the optical element. The controller may be operated automatically, for example where the controller includes an automatic activating device for automatically controlling the amount of voltage applied to the optical element using a photoreceptor/photovoltaic cell configured to provide a voltage proportional to the amount of light impinging on the photoreceptor or where a photoreceptor is configured to provide a signal indicating the amount of light (e.g. sunlight) and selecting a pre-selected set of automatic responses based on the amount of detected light, or using other automatic activation methods known in the art). In other examples, the controller 290 may be operated, activated, or the voltage or other criteria adjusted via a remote control or other wireless devices.

Accordingly, in another aspect, the invention relates to one or more kits that comprise the various elements described herein, including the light attenuating element, the controller, the power source, the means for attaching the optical element, the controller or both, to the viewing lens and/or the eye-shielding device, and, in some cases, a remote control device, and/or an adapter or inverter for recharging the power source (e.g., a USB or similar port and means for connecting it to an outside power source such as a wall socket or car charger).

Also provided herein are methods for attaching an optical insert to a viewing lens of an eye-shielding device. The methods contemplated herein use any of the kits and examples as described above.

Generally, provided herein is a method for attaching an optical insert to a viewing lens of an eye-shielding device, the method includes: providing a viewing lens (10, 110, 210) of an eye-shielding device, providing an optical insert (12, 120, 212) having an outer perimeter (16, 116); providing a border attachment element (14, 114, 214) having an inner periphery area (19, 119) and an outer periphery area (18, 118), as described above, the border attachment element comprising a first adhesive area (20, 120) for attachment to the optical insert and a second adhesive area (22, 122) for attachment to the viewing lens. The method steps include adhering the first adhesive area to the optical insert; and adhering the second adhesive area to the viewing lens of the eye-shielding device so as to create a buffer zone (24, 124) spanning the inner periphery area and the portion of the outer periphery area, as described above.

Adhering the first adhesive areas to the optical insert may include permanently adhering or detachably adhering. Similarly, adhering the second adhesive area to the viewing lens may include permanent adhesion or detachable adhesion. Thus the optical insert and the viewing lens may be either permanently attached or detachably attached, depending on the type of adhesive provided on the first and second adhesive areas.

Where the border attachment element can be stretched, adhering the second adhesive area to the viewing lens may include stretching the border attachment element around a first axis bisecting a width of the optical insert and around a second axis perpendicular to the first axis and bisecting a height of the optical insert, such that the outer periphery of the adhesive area conforms to a curved viewing lens having multiple axes of curvature, or having a different curvature than the optical insert.

Where the kit includes an electronically controlled light attenuating device (such as a liquid crystal cell), the method may further include securing to the viewing lens or the eye-shielding device or its frame, etc., a controller and/or a manually operable activation device electrically connected with the liquid crystal cell for selectively adjusting the voltage across the liquid crystal cell.

Also described herein are viewing lenses of eye-shielding devices assembled with the optical insert and border attachment element of any of the kits, as described above.

In some embodiments, where an electronically controlled light attenuating device is used, the optical insert assembly will include the controller (separate or integrated with the optical insert), and/or an activation device, etc., as described above.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein, all such combinations and sub-combinations are intended to be within the scope of the present inventions. Still further, while various alternative embodiments as to the various aspects, concepts and features of the inventions—such as alternative materials, structures, configurations, methods, circuits, devices and components, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention.

We claim:

1. A kit for attaching an optical insert to a viewing lens of an eye-shielding device, the kit comprising:
    an optical insert having an outer perimeter; and
    a flexible border attachment element having an inner and an outer periphery and comprising a first adhesive area for attachment to the optical insert and a second adhesive area for attachment to the viewing lens,
    wherein at least a portion of the inner periphery of the flexible border attachment element extends inward of the outer perimeter of the optical insert defining an inner periphery area, and at least a portion of the outer periphery of the flexible border attachment element extends outward of the outer perimeter of the optical insert defining an outer periphery area, thereby defining a buffer zone spanning the inner and outer periphery areas
    characterized in that the flexible border attachment element forms a ramp between the optical insert and the viewing lens when the optical insert is attached to the viewing lens by the flexible border attachment element.

2. The kit of claim 1, wherein the buffer zone surrounds the entire outer perimeter of the optical insert.

3. The kit of claim 1, wherein the flexible border attachment element is capable of being stretched so as to permit attachment of the optical insert to a viewing lens with a different curvature than the optical insert.

4. The kit of claim 1, wherein the flexible border attachment element comprises a perforated area.

5. The kit of claim 4, wherein the perforated area comprises a mesh screen having a hole to solid material ratio of from 10:90 to 90:10 or any size in between.

6. The kit of claim 1, wherein at least a portion of the buffer zone comprises a pattern of opaque elements sized and spaced to provide a light filtering effect in the buffer zone.

7. The kit of claim 1, wherein the second adhesive area of the flexible border attachment element comprises an adhesive configured for selective detachment of the flexible border attachment element from the viewing lens of an eye-shielding device.

8. The kit of claim 1, wherein the eye-shielding device is a helmet and the viewing lens is a visor wherein the visor moves in relation to the remainder of the helmet.

9. The kit of claim 1, wherein the optical insert provides an antifog function.

10. The kit of claim 1, wherein the optical insert is a flexible light attenuating element.

11. The kit of claim 10, wherein the light attenuating element comprises an electronically controlled liquid crystal cell and a controller electrically connected to the liquid crystal cell and configured to selectively supply a voltage across the liquid crystal cell.

12. The kit of claim 11, wherein the controller is an integral part of the optical insert.

13. The kit of claim 11, wherein the controller is a separate device configured to be electrically connected to the liquid crystal cell.

14. An optical insert assembly, comprising an optical insert and a flexible border attachment element according to claim 1, attached to a viewing lens of an eye shielding device.

15. A method for attaching an optical insert to a viewing lens of an eye-shielding device, the method comprising:
    providing a viewing lens of an eye-shielding device;
    providing an optical insert and a flexible border attachment element according to claim 1, the border attachment element comprising a first adhesive area for attachment to the optical insert and a second adhesive area for attachment to the viewing lens,
    adhering the first adhesive area to the optical insert;
    adhering the second adhesive area to the viewing lens of the eye-shielding device such that the flexible border attachment element creates a ramp between the optical insert and the viewing lens.

16. The kit of claim 1, wherein the flexible border attachment element has a thickness less than that of the optical insert.

17. The method of claim 15, wherein the optical insert comprises a flexible light attenuating device.

18. The method of claim 17, wherein the flexible light attenuating device is an electronically controlled liquid crystal cell having a controller to selectively supply a voltage to the liquid crystal device.

19. The method of claim 18, wherein the method further comprises securing the controller to the viewing lens or the eye-shielding device.

20. The method of claim 15, wherein adhering the second adhesive area to the viewing lens comprises detachably adhering the outer periphery of the adhesive area to the viewing lens.

* * * * *